| United States Patent [19] | [11] Patent Number: 4,921,964 |
| Bowers, Jr. et al. | [45] Date of Patent: May 1, 1990 |

[54] PROCESS FOR THE PREPARATION OF STILBENE DERIVATIVES

[75] Inventors: Joseph S. Bowers, Jr., Easley, S.C.; Gerald L. Mayberry, Kingsport, Tenn.

[73] Assignee: Eastman Kodak Company, Rochester, N.Y.

[21] Appl. No.: 317,383

[22] Filed: Mar. 1, 1989

[51] Int. Cl.$^5$ .......................................... C07D 413/04
[52] U.S. Cl. ................................................... 548/219
[58] Field of Search ................................. 548/217, 219

[56] References Cited

U.S. PATENT DOCUMENTS

| | | | |
|---|---|---|---|
| 3,360,486 | 12/1967 | Garnish | 260/2 |
| 3,366,575 | 1/1968 | Ono et al. | 252/301.2 |
| 3,407,196 | 10/1968 | Liechti et al. | 260/240 |
| 3,412,089 | 11/1968 | Ohkawa et al. | 260/240 |
| 3,476,747 | 11/1969 | Hargis et al. | 260/240 |
| 3,546,217 | 12/1970 | Siegrist et al. | 260/240 |
| 3,575,996 | 4/1971 | Liecht et al. | 260/307 |
| 3,585,208 | 6/1971 | Rash | 548/217 |
| 3,586,673 | 6/1971 | Bloom et al. | 260/240 |
| 3,641,044 | 2/1972 | Matter | 260/307 |
| 3,678,042 | 7/1972 | Matter | 260/240 |
| 3,682,946 | 8/1972 | Liechti | 548/219 |
| 3,819,615 | 6/1974 | Siegrist | 260/240 |
| 3,860,584 | 1/1974 | Meyer | 260/240 |
| 4,282,253 | 8/1981 | Steck | 424/330 |
| 4,282,355 | 8/1981 | Erckel et al. | 548/217 |
| 4,789,755 | 12/1988 | Van Sickle et al. | 560/78 |

FOREIGN PATENT DOCUMENTS

| | | |
|---|---|---|
| 967569 | 5/1975 | Canada . |
| 967959 | 5/1975 | Canada . |
| 1026368 | 4/1966 | United Kingdom . |
| 1072918 | 6/1967 | United Kingdom . |
| 1081876 | 9/1967 | United Kingdom . |
| 1084136 | 9/1967 | United Kingdom . |
| 1277793 | 6/1972 | United Kingdom . |

OTHER PUBLICATIONS

Chemical Abstracts 17098, vol. 65, 1966 (JP0-6-6-008573).
Chemical Abstracts 55172w, vol. 67, 1967 (JP-6-7-007258).
Chemical Abstracts 88820w, vol. 70, 1969 (JP-6-8-28017).
Chemical Abstracts 107519y, vol. 70, 1969 (JP-6-8-030,193).
Derwent Abstract WPI Acc. No.: 68-72529P/00.
Derwent Abstracty WPI Acc. No.: 75-16708W/10.
Derwent Abstracts WPI Acc. No.: 70-48530R/27.
Derwent Abstract WPI Acc. No.: 70-10184R/07.
Derwent Abstract WPI Acc. No.: 70-10185R/07.
Derwent Abstract WPI Acc. No.: 70-04889R/04.
Derwent Abstract WPI Acc. No.: 70-23429R/14.
Derwent Abstract WPI Acc. No.: 70-77390R/42.
Derwent Abstract WPI Acc. No.: 77-73043Y/41.
Chemical Abstracts 38906h, vol. 70, 1969 (French Patent 1,506,629, Dec. 22, 1967).
Chemical Abstracts 12705h, vol. 72, 1970 (JP-6-9-023,028).
Chemical Abstracts 88821x, vol. 70, 1969 (JP 68-022,790).
Chemical Abstracts 4505g, vol. 71, 1969 (JP-69-00-6-978).
Chemical Abstracts 96811t, vol. 68, 1968 (JP-6-8-000,811).

*Primary Examiner*—Donald G. Daus
*Attorney, Agent, or Firm*—Thomas R. Savitsky; William P. Heath, Jr.

[57] ABSTRACT

Disclosed is a process for the preparation of stilbene compounds such as bis(2-benzoxazolyl) stilbenes by reacting a stilbenedicarboxylate such as dimethyl-4,4'-stilbenedicarboxylate with an o-aminophenol in an organic solvent such as chloronaphthalene in the presence of a catalytic amount of a tin or titanium compound. The reaction is typically carried out at a temperature of about 200°–250° C. and a preferred catalyst is either dibutyl tin oxide or titanium tetra-alkoxide.

22 Claims, No Drawings

PROCESS FOR THE PREPARATION OF STILBENE DERIVATIVES

FIELD OF THE INVENTION

The present invention is directed to a process for the preparation of certain stilbene derivatives which are useful as fluorescent brightening agents and light stabilizers for polyolefin and polyester fibers and shaped articles.

BACKGROUND OF THE INVENTION

Prior art processes for the preparation of certain stilbene derivatives, particularly certain 4,4'-bis(substituted-2-benzoxazolyl)stilbenes, can be placed into three types of processes.

The first type of process produces symmetrical compounds which involves the formation of both benzoxazole rings prior to the formation of the stilbene nucleus. Such processes are disclosed in, for example, British Patent 1,072,918; Japanese Patent 66-018,838; and U.S. Pat. Nos. 3,546,217; 3,476,747; and 3,819,615.

The second type of process produces unsymmetrical compounds which involves formation of the stilbene nucleus in between the formation of the two differently substituted benzoxazole rings, or the formation of the stilbene nucleus by the combination of two differently substituted precursors in a selective manner. Such processes are disclosed in, for example, Belgian Patent 659,078; Japanese Patents 70-002,669; 70-002,670; 69-006,978; and U.S. Pat. Nos. 3,586,673; and 3,407,196.

The third type of process produces symmetrical compounds which involves the formation of the stilbene nucleus prior to the formation of both benzoxazole rings. Such processes are disclosed in, for example, Japanese Patents 68-000,811; 66-008,573; 68-028,017; 68-030,193; 70-000,771; South African Patent 68-005,356; French Patent 1,397,727; Belgian Patents 641,426; 651,310; and U.S. Pat. Nos. 3,412,089; 3,575,996; 3,366,575; 3,860,584; 3,585,208.

Dimethyl or diethyl-4,4'-stilbenedicarboxylate has been used as a starting material in the process disclosed in U.S. Pat. No. 3,412,089. This process involves condensing the dialkyl-4,4'-stilbenedicarboxylate with an appropriate o-aminophenol in polyphosphoric acid at 200°–230° C. for 8 hours, cooling to 100° C., pouring into water and filtering. Heating the crude solid in 5% aqueous sodium hydroxide solution, filtering and washing with water gives the final product in reported 95% yield.

It is also known that 2-(p-tolyl)benzoxazole compounds are produced by the direct reaction of methyl-p-toluate with o-aminophenol at an elevated temperature in the presence of a catalytic amount of a tin or titanium compound. However, in the case where dimethyl-4,4'-stilbenedicarboxylate is used instead of methyl-p-toluate in the above direct reaction, we have found that the conversion is low and unsatisfactory for an industrial process. Even when typical industrial solvents are employed that boil below about 200° C. (e.g., benzene, toluene, xylene, chlorobenzene, dimethyl sulfoxide) we have found that conversions remain low.

SUMMARY OF THE INVENTION

The present invention is directed to a process for preparing stilbene compounds of the formula:

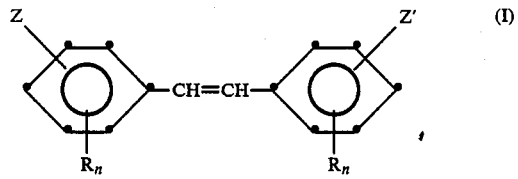

wherein each of Z and Z' is independently of one another

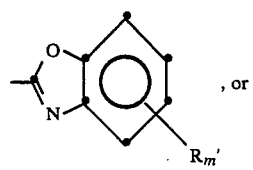

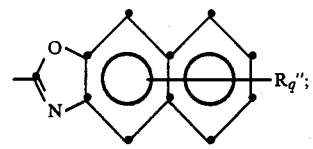

each of R, R', and R" is independently of one another halo, $C_1$–$C_{12}$ alkyl, cyano, $C_1$–$C_4$ alkylsulfonyl, $C_7$–$C_9$ alkylaryl, or $C_6$–$C_{10}$ aryl; each of n and m is independently of one another an integer of 0–4; and q is an integer of 0–6; provided that:

the R substituents on one ring are the same as on the other ring; the substitution pattern of the R, Z and Z' substituents on one ring is symmetrical to the other ring; and each n is the same;

said process comprising contacting a stilbenedicarboxylate compound of the formula

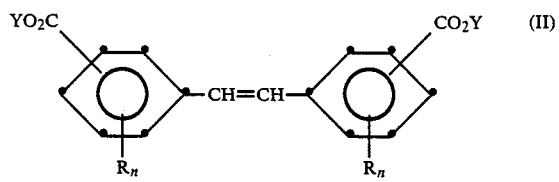

wherein each R and n has the same meaning as defined above; and each Y is a $C_1$–$C_8$ alkyl; provided that the substitution pattern of the R and —$CO_2Y$ substituents on one ring is symmetrical to the other ring; the R and Y substituents on one ring are the same as on the other ring; and each n is the same;

with one or two ortho-aminohydroxy aromatic compounds of the formula:

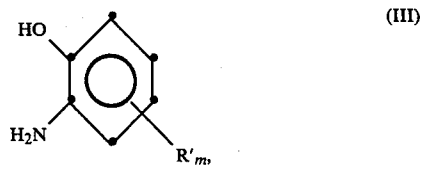

or

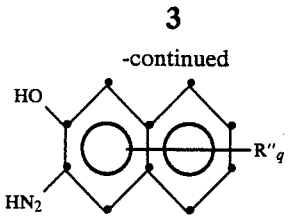

wherein R', R", m, q have the same meaning as defined above;

in an organic solvent that boils above about 200° C., in the presence of a catalytic amount of a compound of tin or titanium, and at a reaction temperature and for a reaction time sufficient to promote the formation of the desired product.

A preferred process of the present invention is carried out in two steps wherein a first step is carried out wherein a stilbenedicarboxylate compound is reacted with about 1–1.2 molar equivalents of a first ortho-aminohydroxy aromatic compound to form an intermediate reaction mixture containing a stilbene monocarboxylate compound of the formula

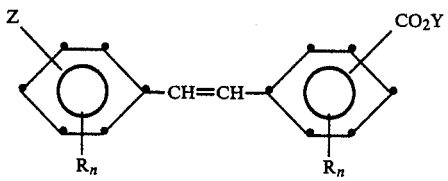

wherein R, n, Z and Y have the same meaning as previously defined; followed by a second step wherein said stilbene monocarboxylate compound is reacted with about 1–1.2 molar equivalents of a second, different ortho-aminohydroxy aromatic compound under conditions such that a desired unsymmetrical stilbene compound is formed.

Another preferred embodiment of the present invention can be described as a process for preparing a stilbene compound of the formula

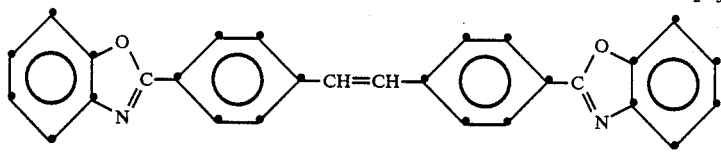

comprising contacting dimethyl-4,4'stilbenedicarboxylate with ortho-aminophenol in a suitable organic solvent in the presence of a compound of tin or titanium at a reaction temperature and for a reaction time sufficient to promote the formation of the desired product.

DETAILED DESCRIPTION OF THE INVENTION

The alkyl groups described herein can be straight chain, branched, or, where appropriate, cyclic. Preferred alkyl groups contain 1 to 8 carbon atoms, and the most preferred alkyl groups are methyl and ethyl. The term "alkylaryl" is meant to include $C_1$–$C_3$ alkyl groups substituted at any position with a phenyl or substituted phenyl moiety; an example of such a group is benzyl. Preferred aryl groups are phenyl, naphthyl, substituted phenyl or substituted naphthyl. The substituents on the aryl groups can be one, two, or three substituents such as $C_1$–$C_{12}$ alkyl, halo, cyano, $C_1$–$C_4$ alkylsulfonyl, $C_7$–$C_9$ alkylaryl, or $C_6$–$C_{10}$ aryl. There can be one, two, three, or four R substituents on each benzene ring of the stilbene moiety; however, it is preferred that both benzene rings of the stilbene moiety have no R substituents. Additionally, there can be one, two, three or four R' moieties on each benzoxazolyl moiety, but it is preferred that there are no R' moieties. Likewise, there can be one, two, three, four, five or six R" substituents on each naphthyl-containing moiety, but it is preferred that there are no R" moieties.

What is meant by the substitution being symmetrical is that the Z and Z' substituents must be in the corresponding positions on each ring such as in the 2,2', 3,3', or 4,4' positions; preferred are the 4,4' positions. Similarly, the R substituent on one ring must occupy the corresponding position on the other ring. Examples of the above include the following:

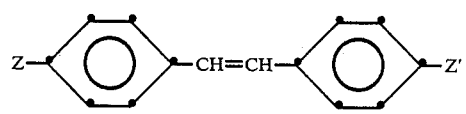

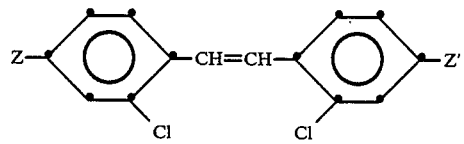

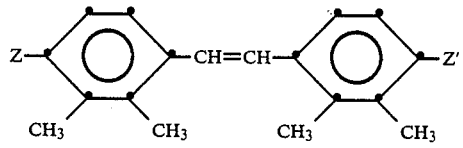

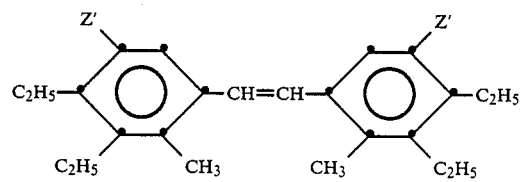

The stilbene compounds used in the present invention can be in either the cis or trans form, preferred is trans.

Suitable organic solvents for use in the present invention are those that boil above about 200° C. and are substantially unreactive toward reactants, products and catalyst. Another property of suitable organic solvents that is preferred but not necessary is that they are liquid at or near room temperature. Preferred organic solvents are naphthalene derivatives. Such solvents preferably solubilize impurities such that after filtration and a simple washing away of the reaction solvent no further purification is needed. Specific examples of suitable organic solvents include methylnaphthalene, dimethylnaphthalene, chloronaphthalene, naphthalene, biphenyl, phenyl ether, bibenzyl toluene, diphenyl ethane, alkyl substituted diphenylethanes such as 1,1-di(o- xylyl)ethane, and any mixture of two or more thereof. Preferred solvents contain a naphthyl moiety. It is preferred that only one or two different ortho-aminohydroxy aromatic compounds (Compound III or Compound IV) are used as reactant(s) in the process of the present invention. Specific examples of such compounds include ortho-aminophenol, 3-methyl-2-aminophenol, 4-methyl-2-aminophenol, 5-methyl-2-aminophenol, 6-methyl-2-aminophenol, 4,5-dimethyl-2-aminophenol, 3-chloro-2-aminophenol, 4-bromo-2-aminophenol, 5-fluoro-2-aminophenol, 6-cyano-2-aminophenol, 3-methylsulfonyl-2-aminophenol, or 5-butylsulfonyl-2-aminophenol.

A preferred stilbenedicarboxylate compound (Compound II) is dimethyl-4,4'-stilbenedicarboxylate.

The process of this invention can be carried out either continuously or batchwise. Either way it is preferred that the reaction is carried out in such a way that the water and the alcohol formed during the course of the reaction are continuously removed from the reaction zone. By-product water and alcohols can usually be removed by a slow stream of inert gas (e.g., $N_2$ or argon) or in some cases by the limited addition of an entraining agent such as toluene or xylene at a rate slow enough such that the vaporization of the entraining agent does not lower the temperature in the reaction zone. A typical reaction temperature range for the process of the present invention is about 150° to 350° C.; preferred is about 200° to 275° C.; more preferred is about 225° to 250° C. Stoichiometrically equivalent quantities of the reactants or an excess of either reactant can be used in the present reaction, where a stoichiometric equivalence is a molar ratio of Compound II to Compound III and/or IV of 1:2. However, a molar excess of either type of reactant is possible. When an excess of Compound II is used (i.e., >1:2) an appreciable quantity of a mono-carboxylic stilbene derivative may be produced. This aspect of the invention allows for the preparation of a Compound I that is unsymmetrical.

By using differently substituted o-aminophenols either simultaneously or in sequence, mixtures of symmetrical and unsymmetrical compounds within the scope of Compound I can be produced with widely varying ratios of components. For producing the symmetrical 4,4'-bis(substituted-2-benzoxazolyl)stilbene the preferred ratio of dialkyl-4,4'-stilbenedicarboxylate to o-aminophenol is about 1:2 to 1:3.

This process can be carried out at atmospheric pressure, below or above atmospheric pressure. For convenience, it is preferred to carry out the process at atmospheric pressure.

It is preferred that the process of the present invention yield at least 70% of the theoretical maximum of desired product(s), more preferred is at least 90%.

The tin and titanium compounds which can be used as a catalyst in the present process are well known as esterification, polyesterification, alcoholysis, acidolysis, and benzoxazolation catalysts. These compounds are disclosed in U.S. Pat. No. 3,585,208 and references therein. Especially preferred among the titanium compounds are the titanium tetra-alkoxides, especially those in which the alkyl moieties contain 1 to about 8 carbon atoms, such as titanium tetraisopropoxide. Also preferred are dialkyl tin compounds having one to eight carbon atoms per alkyl group. A catalytic amount of the compound of titanium or tin is a weight ratio of catalyst:compound II of about 1:2-200; preferred is about 1:10-30.

The starting materials for use in the process of the present invention can be made by techniques known in the art. It is preferred that the stilbene dicarboxylate compound starting material (Compound II) is prepared by reacting a toluate ester derivative with elemental sulfur as described in, for example, U.S. Pat. No. 4,789,755. The ortho-aminophenol compounds can be made by the methods well-known in the art.

The following examples illustrate the present invention but should not be interpreted as a limitation thereon.

EXAMPLE 1 (Comparative)

To a nitrogen purged, stirred 250 ml flask fitted with a condenser and a Dean-Stark trap were added 10.4 g (0.035 mole) of dimethyl-4,4'-stilbenedicarboxylate, 10.0 g (0.092 mole) of o-aminophenol, 200 g of o-dichlorobenzene and 1.0 g of titanium tetraisopropoxide. The mixture was heated at reflux (180°–183° C.) for 4 hours. No water was collected in the Dean-Stark trap. The reaction mixture was cooled to 20°–25° C., filtered, washed with acetone, and dried. Liquid chromatographic analysis indicated that no 4,4'-bis(2-benzoxazolyl)stilbene was produced.

EXAMPLE 2 (Comparative)

Example 1 was repeated on the same scale using 200 g of xylene as solvent instead of o-dichlorobenzene. This reaction also did not produce 4,4'-bis(2-benzoxazolyl)stilbene.

EXAMPLE 3 (Comparative)

To a nitrogen purged, stirred 500 ml stainless steel autoclave were added 10.4 g (0.035 mole) of dimethyl-4,4'-stilbenedicarboxylate, 10.0 g (0.092 mole) of o-aminophenol, 200 g of xylene and 0.5 g titanium tetraisopropoxide. The autoclave was sealed, purged, and pressurized with nitrogen to 120 psig. The contents of the autoclave were heated to 240°–245° C. and held at 240°–245° C. for 4 hours. After cooling, the contents of the autoclave were discharged, filtered, washed with isopropyl alcohol, and dried to give 11.5 g of a brown solid (65.5% assay). The yield of 4,4'-bis(2-benzoxazolyl)stilbene was only 52.7% based on dimethyl-4,4'-stilbenedicarboxylate.

EXAMPLE 4

Example 1 was repeated on the same scale using 200 g of diphenyl ether as solvent instead of o-dichlorobenzene. The mixture was heated to 220°–225° C. and held for 2 hours then further heated to 260°–265° C. while removing low boilers. After 2 hours at 260°–265° C. the reaction was cooled to 130° C. and 400 ml of xylene was added. Filtering at 120° C., washing with xylene, and drying gave 14.2 g of brown-green solid (93.6% assay). The yield of 4,4'-bis(2-benzoxazolyl)stilbene was 91.7% based on dimethyl-4,4'-stilbenedicarboxylate.

EXAMPLE 5

To a nitrogen purged, stirred 250 ml flask fitted with a reflux condenser were added 10.4 g (0.035 mole) of dimethyl-4,4'-stilbenedicarboxylate, 8.0 g (0.073 mole) of o-aminophenol, 200 g of naphthalene, and 0.5 g of titanium tetraisopropoxide. The mixture was heated to reflux (218°–220° C.) with steam on the condenser and run for 18 hours, cooled to 100° C., diluted with heptane and toluene. The precipiate was filtered, washed with isopropyl alcohol, and dried to give 14.7 g of a bright yellow solid (99.0% assay). The yield of 4,4'-bis(2-benzoxazolyl)stilbene was 99.4% based on dimethyl-4,4'-stilbenedicarboxylate.

EXAMPLE 6

Example 5 was repeated on the same scale using 200 g of 1-chloronaphthalene as solvent instead of naphthalene. The mixture was heated to and held at 245°–250° C. and 4 hours, cooled to 120° C., diluted with 300 ml xylene, filtered at 50° C., washed with isopropyl alcohol, and dried to give 13.9 g of a bright yellow solid (100% assay). The yield of 4,4'-bis(2-benzoxazolyl)stilbene was 95.8% based on dimethyl-4,4'-stilbenedicarboxylate.

EXAMPLE 7

Example 6 was repeated on the same scale, conditions and work-up using 200 g of methylnaphthalene (mixed isomers) as solvent instead of 1-chloronaphthalene. The reaction produced 14.0 g of bright yellow solid (97.4% assay). The yield of 4,4'-bis(2-benzoxazolyl)stilbene was 94.0% based on dimethyl-4,4'-stilbenedicarboxylate.

EXAMPLE 8

To a nitrogen purged, stirred 1.01 flask fitted with condenser and a Dean-Stark trap were added 89.0 g (0.30 mole) of dimethyl-4,4'-stilbenedicarboxylate, 84.0 g. (0.77 mole) of 2-amino-p-cresol, 500 g of methylnaphthalene (mixed isomers), and 5.0 g of titanium tetraisopropoxide. The mixture was heated to 240° C. over 1½ hours and held at 240°–245° C. for 2½ hours. The reaction mixture was cooled to 150° C., diluted with 250 ml xylene, filtered at 100° C., washed with DMF and then acetone, and dried to give 112.0 g of a bright yellow solid (98.0% assay). The yield of 4,4'-bis(5-methyl-2-benzoxazolyl)stilbene was 84.5% based on dimethyl-4,4'-stilbenedicarboxylate.

EXAMPLE 9

To a nitrogen purged, stirred 250 ml flask fitted with a condenser and a Dean-Stark trap were add 31.0 g (0.104 mole) of dimethyl-4,4'-stilbenedicarboxylate, 27.8 g (0.255 mole) of o-aminophenol, 125 g of methylnaphthalene (mixed isomers) and 1.5 g of dibutyl tin oxide. The mixture was heated to 240° C. over 1½ hours and held at 240°–245° C. for 2½ hours. The reaction mixture was cooled to 150° C., diluted with 50 ml DMF, refluxed for 1 hour, filtered at 100° C., washed with DMF then acetone, and dired to give 36.0 g of a bright yellow solid (98.9% assay). The yield of 4,4'bis(2-benzoxazolyl)stilbene was 86.3% based on dimethyl-4,4'-stilbenedicarboxylate.

EXAMPLE 10

To a nitrogen purged, stirred 1.01 flask fitted with a condenser and a Dean-Stark trap were added 62.3 g (0.21 mole) of dimethyl-4,4'-stilbenedicarboxylate, 27.5 g (0.25 mole) of o-aminophenol, 20.7 g (0.17 mole) 2-amino-p-cresol, 3.0 g of titanium tetraisopropoxide, and 250 g. of methylnaphthalene (mixed isomers). the mixture was heated to 240° C. over 1½ hours and held at 240°–245° C. for 2 hours. The reaction mixture was cooled to 150° C., diluted with 100 ml DMF, refluxed 30 minutes, filtered at 100° C., washed with DMF then acetone, and dried to give 55.0 g. of a bright yellow solid. Liquid chromatographic analysis indicated a mixture of 37.5% 4,4'-bis(2-benzoxazolyl)stilbene, 45.2% 4-(5-methyl-2-benzoxazolyl)-4'-(2-benzoxazolyl)stilbene and 15.2% 4,4'-bix(5-methyl-2-benzoxazolyl)stilbene.

EXAMPLE 11

To a nitrogen purged, stirred 250 ml flask fitted with a condenser and a Dean-Stark trap were added 29.6 g. (0.10 mole) of dimethyl-4,4'-stilbenedicarboxylate, 21.8 g (0.20 mole) of o-aminophenol, 100 g. of methylnaphthalene (mixed isomers, and 3.0 g of titanium tetraisopropoxide. The mixture was heated to 240° C. for 5 minutes. The reaction mixture was cooled to 150° C., diluted with xylene, and filtered at 100° C. The filtrate was cooled to 20°–25° C., diluted with acetone, filtered, washed with acetone, and dried to give 20 g of a tan solid. Liquid chromatographic analysis indicated a mixture of 82.0% methyl-4-(2-benzoxazolyl)stilbene-4'-carboxylate, 12.8% 4,4'-bis(2-benzoxazolyl)stilbene and 4.0% dimethyl-4,4'-stilbenedicarboxylate.

EXAMPLE 12

To a nitrogen purged, stirred 250 ml flask fitted with a condenser and a Dean-Stark trap were added 35.5 g (0.10 mole) of methyl-4-(2-benzoxazolyl)stilbene-4'-carboxylate, 13.5 g (0.11 mole) of 2-amino-p-cresol, 100 g. of methylnaphthalene and 1.0 g of titanium tetraisoproxide. The mixture was heated slowly to 240° C. and held at 240°–245° C. for 1 hour. The reaction mixture was cooled to 150° C., diluted with 100 ml xylene and 30 ml DMF, filtered at 100° C., washed with DMF then acetone, and dried to give 32 g of a bright yellow solid. The liquid chromatographic analysis indicated a mixture of 86.1% 4-(5-methyl-2-benzoxazolyl)-4'-(2-benzoxazolyl)stilbene, 8.4% 4,4'-bis(2-benzoxazolyl)stilbene, 3.3% 4,4'-bis(5-methyl-2-benzoxazolyl)stilbene, and 1.2% dimethyl-4,4'-stilbenedicarboxylate.

The invention has been described in detail with particular reference to preferred embodiments thereof, but it will be understood that variations and modifications can be effected within the spirit and scope of the invention. All of the U.S. Patents cited herein are incorporated herein by reference in their entirety.

We claim:

1. A process for preparing stilbene compounds of the formula:

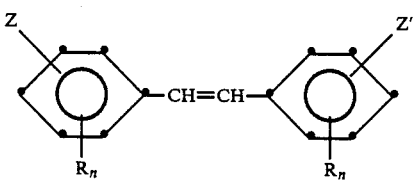

wherein each of Z and Z' is independently of one another

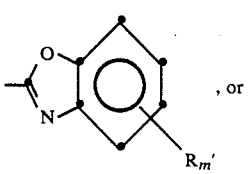

, or

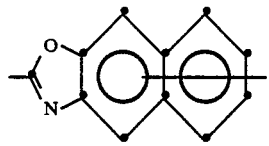

each of R, R', and R" is independently of one another halo, $C_1$–$C_{12}$ alkyl, cyano, $C_1$–$C_4$ alkylsulfonyl, $C_7$–$C_9$ alkylaryl, or $C_6$–$C_{10}$ aryl; each of n and m is independently of one another an integer of 0–4; and q is an integer of 0–6; provided that:

the R substituents on one ring are the same as on the other ring; the substitution pattern of the R, Z and Z' substituents on one ring is symmetrical to the other ring; and each n is the same;

said process comprising contacting a stilbenedicarboxylate compound of the formula

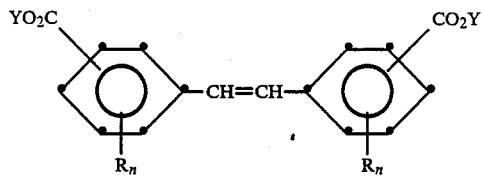

wherein each R and n has the same meaning as defined above; and each Y is a $C_1$–$C_8$ alkyl; provided that the substitution pattern of the R and —$CO_2Y$ substituents on one ring is symmetrical to the other ring; the R and Y substituents on one ring are the same as on the other ring; and each n is the same;

with one or two ortho-aminohydroxy aromatic compounds of the formula:

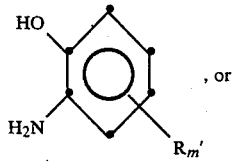

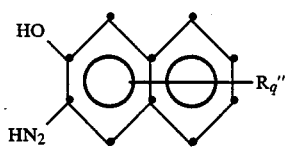

wherein R', R", m, q have the same meaning as defined above;

in an organic solvent that boils above about 200° C., in the presence of a catalytic amount of a compound of tin or titanium, and at a reaction temperature and for a reaction time sufficient to promote the formation of the desired product.

2. The process of claim 1 wherein said organic solvent is methylnaphthalene, dimethylnaphthalene, chloronaphthalene, naphthalene, biphenyl, phenyl ether, bibenzyl toluene, diphenyl ethane, alkyl substituted diphenylethanes, or any mixture of two or more thereof.

3. The process of claim 1 wherein said compound of tin or titanium is a titanium tetraalkoxide having one to eight carbon atoms per alkyl group or a dialkyl tin oxide having one to eight carbon atoms per alkyl group.

4. The process of claim 1 wherein said reaction temperature is about 150°–350° C. and said reaction time is about 1–24 hours.

5. The process of claim 1 wherein said reaction temperature is about 225°–275° C.

6. The process of claim 1 wherein the molar ratio of said stilbenedicarboxylate compound to said ortho-aminohydroxy aromatic compound is about 1:2 to 1:3.

7. The process of claim 1 wherein the stilbene dicarboxylate compound is prepared by reacting a toluate compound with elemental sulphur.

8. The process of claim 1 wherein water and alcohol are removed during the reaction.

9. The process of claim 1 wherein Z and Z' are the same and one ortho-aminohydroxy aromatic compound is used as a reactant.

10. The process of claim 1 wherein Z and Z' are different and two different ortho-aminohydroxy aromatic compounds are used as reactants.

11. The process of claim 10 carried out in two steps wherein a first step is carried out wherein a stilbenedicarboxylate compound is reacted with about 1–1.2 molar equivalents of a first ortho-aminohydroxy aromatic compound to form an intermediate reaction mixture containing a stilbene monocarboxylate compound of the formula

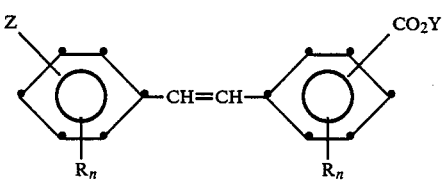

wherein R, n, Z and Y have the same meaning as previously defined; followed by a second step wherein said stilbene monocarboxylate compound is reacted with about 1–1.2 molar equivalents of a second, different ortho-aminohydroxy aromatic compound under conditions such that a desired unsymmetrical stilbene compound is formed.

12. The process of claim 1 wherein the ortho-aminohydroxy aromatic compound is ortho-aminophenol, 3-methyl-2-aminophenol, 4-methyl-2-aminophenol, 5-methyl-2-aminophenol, 6-methyl-2-aminophenol, 4,5-dimethyl-2-aminophenol, 3-chloro-2-aminophenol, 4-bromo-2-aminophenol, 5-fluoro-2-aminophenol, 6-cyano-2-aminophenol, 3-methylsulfonyl-2-aminophenol, or 5-butylsulfonyl-2-aminophenol; and the stilbenedicarboxylate compound is dimethyl-4,4'-stilbenedicarbonylate.

13. The process of claim 11 wherein said first and second ortho-aminohydroxy aromatic compounds are selected from the group consisting of ortho-aminophenol, 3-methyl-2-aminophenol, 4-methyl-2-aminophenol, 5-methyl-2-aminophenol, 6-methyl-2-aminophenol, 4,5-dimethyl-2-aminophenol, 3-chloro-2-aminophenol, 4-bromo-2-aminophenol, 5-fluoro-2-aminophenol, 6-cyano-2-aminophenol, 3-methylsulfonyl-2-aminophenol, and 5-butylsulfonyl-2-aminophenol; and the stilbenedicarboxylate compound is dimethyl-4,4'-stilbenedicarboxylate.

14. A process for preparing a stilbene compound of the formula

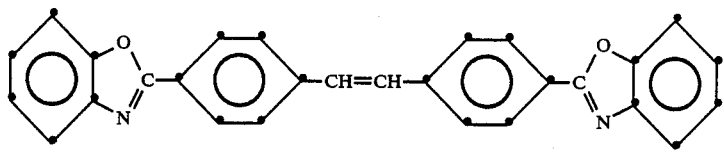

comprising contacting dimethyl-4,4'stilbenedicarboxylate with ortho-aminophenol in an organic solvent that boils above about 200° C., in the presence of a compound of tin or titanium, and at a reaction temperature and for a reaction time sufficient to promote the formation of the desired product.

15. The process of claim 14 wherein said organic solvent is methylnaphthalene, dimethylnaphthalene, chloronaphthalene, naphthylene, biphenyl, phenyl ether, bibenzyl toluene, diphenyl ethane, alkyl substituted diphenylethanes, or any mixture of two or more thereof.

16. The process of claim 14 wherein said compound of tin or titanium is a titanium tetraalkoxide having one to eight carbon atoms per alkyl group or a dialkyl tin oxide having one to eight carbon atoms per alkyl group.

17. The process of claim 14 wherein said reaction temperature is about 150°–350° C. and said reaction time is about 1–24 hours.

18. The process of claim 14 wherein said reaction temperature is about 225°–275° C.

19. The process of claim 14 wherein the molar ratio of dimethyl-4,4'stilbenedicarboxylate to ortho-aminophenol is about 1:2 to 1:3.

20. The process of claim 14 wherein said organic solvent is diphenyl ether, naphthalene, 1-chloronaphthalene, methylnaphthalene, or any mixture of two or more thereof.

21. The process of claim 14 wherein dimethyl-4,4'-stilbenedicarboxylate is prepared by reacting methyl p-toluate with elemental sulphur.

22. The process of claim 14 wherein alcohol and water are removed during the reaction.

* * * * *